United States Patent [19]
Kocanowski

[11] Patent Number: 4,471,942
[45] Date of Patent: Sep. 18, 1984

[54] IN-LINE VALVE FOR ADMINISTERING PARENTERAL LIQUIDS
[75] Inventor: Stephen Kocanowski, Middlesex, N.J.
[73] Assignee: Whitman Medical Corporation, Clark, N.J.
[21] Appl. No.: 421,830
[22] Filed: Sep. 23, 1982
[51] Int. Cl.³ .................. F16K 35/02; F16K 3/32
[52] U.S. Cl. ........................... 251/205; 251/212; 251/326; 251/327; 251/DIG. 5; 251/115; 604/33; 604/249
[58] Field of Search .......... 251/205, 327, DIG. 5, 251/212, 326, 111, 115; 604/32, 33, 248, 249

[56] References Cited
U.S. PATENT DOCUMENTS

| | | |
|---|---|---|
| 1,176,100 | 3/1916 | Ronk . |
| 1,770,717 | 7/1930 | Stremberger ............... 251/205 X |
| 1,805,106 | 5/1931 | Robinson ..................... 251/205 |
| 1,847,011 | 2/1932 | Kratzer ...................... 251/327 X |
| 1,892,260 | 12/1932 | Wick .......................... 251/205 X |
| 2,112,913 | 4/1938 | Lechene . |
| 2,596,817 | 5/1952 | McGovney ................ 251/326 X |
| 3,212,753 | 10/1965 | Milette . |
| 3,305,207 | 2/1967 | Calderoni et al. . |
| 3,938,779 | 2/1976 | Benjamin ................... 251/327 X |
| 4,161,307 | 7/1979 | Clinch et al. . |
| 4,230,300 | 10/1980 | Wiltse ........................ 251/205 |
| 4,332,369 | 6/1982 | Gordon et al. ............. 251/205 X |

FOREIGN PATENT DOCUMENTS

| | | | |
|---|---|---|---|
| 1918875 | 11/1969 | Fed. Rep. of Germany ...... 251/326 |
| 1028022 | 5/1966 | United Kingdom ............ 251/327 |
| 2073374 | 10/1981 | United Kingdom ............ 251/326 |

Primary Examiner—Arnold Rosenthal
Attorney, Agent, or Firm—Holman & Stern

[57] ABSTRACT

An intravenous flow control valve includes in-line valving mechanism wherein flow through the valve at low flow settings increases slowly with displacement of a valve controller disc. The disc, which is free to rotate with respect to an axis but is longitudinally fixed, includes a threaded stem which engages a threaded bore and a sluice gate member. The gate member is permitted to move only longitudinally in a valve control chamber in response to disc rotation and includes a control passage defined therethrough which tapers in the direction of gate member motion so as to graduate the cross-sectional area of the passage exposed to flow as the disc rotates. A locking arrangement permits the disc to be positionally locked to avoid inadvertent change of the valve setting. The disc and stem provide an hermetic seal for the valve control chamber to avoid contamination of the intravenous fluid being controlled.

15 Claims, 22 Drawing Figures

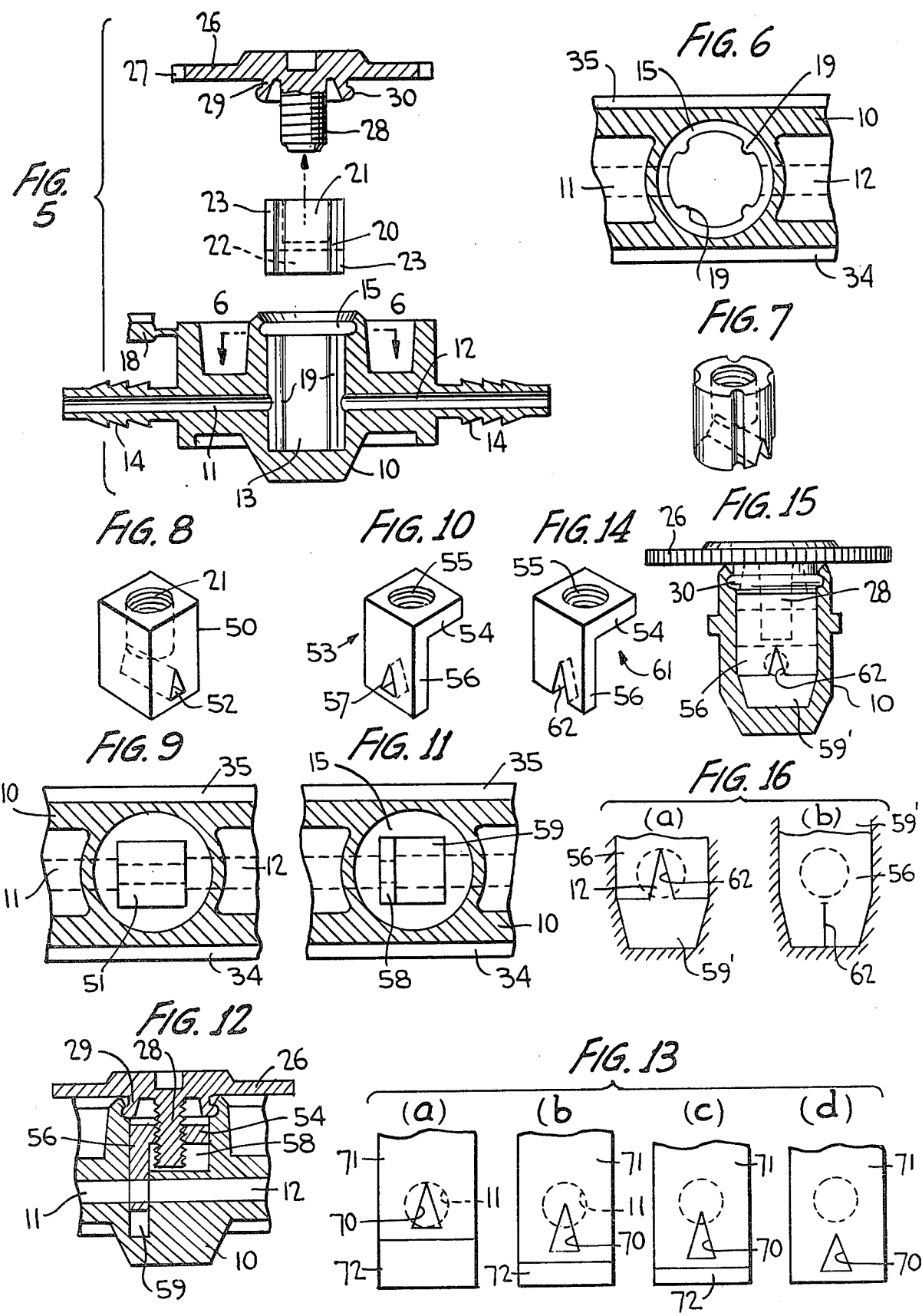

IN-LINE VALVE FOR ADMINISTERING PARENTERAL LIQUIDS

BACKGROUND OF THE INVENTION

1. Technical Field

The present invention relates to control valves in systems with parenteral fluid infusion. More specifically, the present invention relates to a valve which, although simple and inexpensive to manufacture, permits accurate and reliable adjustable settings at intravenous liquid flow rates.

2. Prior Art

In U.S. Pat. No. 4,332,369 to Gordon et al. there is disclosed an in-line valve for use in controlling flow of intravenous fluid. The valve employs a sluice-type gate member which is selectively reciprocated longitudinally in a control chamber by rotation of a disc member having a stem which threadedly engages a bore in the gate member. Reciprocation of the gate member varies communication between inlet and outlet passages of the chamber. The rotational position of the disc is selectively locked to preclude inadvertent changes of the valve setting by forcing a bearing surface radially against the disc periphery and snap-locking the bearing surface in place. The disclosure of the aforesaid U.S. Pat. No. 4,332,369 is expressly incorporated herein by reference in its entirety.

A modification of the valve disclosed in the aforesaid U.S. Pat. No. 4,332,369 is the subject of U.S. patent application Ser. No. 377,429, filed May 12, 1982 by Gordon et al. and entitled "Adjustable In-Line Valve for Sterile Fluids", the disclosure of which is also expressly incorporated herein by reference in its entirety. That modification involves providing a hermetic seal for the control chamber so as to avoid the potential for contamination of intravenous fluid through the gate member. Specifically, the disc is captured in an annular snap-fit in the control chamber so that the disc is free to rotate but not to move axially. The snap-fit seals the chamber from the ambient environment.

The gate member for the valve in the aforementioned Gordon et al. patent and patent application is of the sluice type having an arcuate edge or surface extending transversely of gate member movement and which is moved perpendicular to flow between the valve inlet and outlet passages across a controlled chamber. It has been found that, while these valves provide the desired locking feature and hermetic sealing, the flow control varies rapidly with respect to even small disc rotation throughout the control range of interest. More specifically, in administering parenteral fluid, the usual range of flow rate is from less than 1 to approximately 4 cc per minute. It is quite difficult to accurately vary flow rates within this range of interest with the valves described above. This can best be understood by envisioning a circular opening of the valve inlet passage into the control chamber and a sluice plate having a concave bottom edge being gradually moved to open or unblock more and more of the circular opening. The unblocked portion or flow area of the opening has a crescent or a convexo-concave configuration which varies in thickness as the gate member moves. It can be shown that this crescent-shaped flow area varies as a complex curve function of gate member displacement and provides very little control accuracy over the low flow rates (i.e. below 4 cc per minute) which are of interest in most parenteral liquid administration procedure.

One solution to the problem stated above would be to decrease the pitch in the threaded engagement between the valve stem and bore so that more turns of the disc are required to achieve a given change in flow rate. However, the valve must be able to quickly purge air from the intravenous line and to be quickly adjusted to deliver high flow rates in emergency conditions. If the stem and the bore thread pitch were decreased sufficiently to provide the desired control at low flow rate, the transition from low to high flow rate would require too many rotations of the disc to be useful in an emergency situation.

OBJECTS AND SUMMARY OF THE INVENTION

It is therefore an object of the present invention to provide a valve for controlling administration of parenteral liquids which permits accurate control of the deliberate flow at the low flow rates at which such liquids are normally delivered.

It is another object of the present invention to provide a control valve for use with an I.V. (intravenous) set wherein adjustment of the valve actuated produces relatively small changes in flow rate at the low flow rates which are normally used for administering parenteral liquids. In addition, it is an object of the present invention to provide such valve with the ability to quickly change to a high-flow rate mode to permit purging of the line and emergency delivery of high-flow rates.

It is another object of the present invention to provide a control valve of the type described having parts which are easily and inexpensively fabricated.

In accordance with the present invention, the gate member of the valve described in the aforementioned U.S. Pat. No. 4,332,369 (Gordon at al.) and U.S. patent application Ser. No. 377,429 (Gordon et al.) is modified to provide a flow communication area which varies with gate member displacement in a manner to achieve the aforesaid object. Different variations in gate member configuration were considered but dismissed as either not providing the desired flow control characteristics or being too difficult and expensive to fabricate. I have found that the gate member can be simply and inexpensively contoured to provide a genuinely parabolic flow vs. displacement characteristic. The parabola can be contoured by parameter selection to provide a relatively slow change of flow rate with valve displacement at low flow rates, and to provide a relatively large flow rate change for valve displacement at higher flow rates. The optimum gate configuration for achieving a parabolic function without sacrificing fabrication simplicity and low cost is a gate passage of substantially triangular cross-section. The triangular passage can be defined as a groove or notch in the edge surface of the gate or as a bore defined through the gate. The gate member itself may be cylindrical about an axis defining gate movement within a concentric cylindrical controlled chamber. The gate member, under such circumstances, slidably engages the control chamber wall to permit mutual longitudinal displacement but not rotational displacement. Alternatively, the gate member and the chamber may have matched polygonal cross-sections to permit longitudinal sliding without rotation of the gate member within the chamber. In any case, the juxtaposition of a translatable substantially triangular opening and a flow passage of arcuate section results in a substantially parabolic flow vs. gate displacement characteristic in which the range of small flow change vs. displacement can be made large or small by selecting the apex angle of the triangular opening accordingly.

The valve further includes a handle member into which the remainder of the assembly can be inserted in a snap-fit. A latch or handle is adapted to receive a mating projection of a flap formed as part of the valve's body to latch a bearing surface of the flap against the disc controller to prevent inadvertent movement of the disc.

BRIEF DESCRIPTION OF THE DRAWINGS

In the above and still further objects, features and advantages of the present invention will become apparent upon consideration of the following detailed description of the specific embodiments thereof, especially when taken in conjunction with the acompanying drawings, wherein:

FIG. 5 is a partially exploded side view in section of the valve of FIGS. 1 through 4;

FIG. 6 is a view in section taken along on 6—6 of FIG. 5 and showing the control chamber of the valve in detail;

FIG. 7 is a view in perspective of the gate member of the valve of FIGS. 1 through 6;

FIG. 8 is a view in perspective of an alternative gate member construction according to the present invention;

FIG. 9 is a view in section similar to FIG. 6 but showing a control chamber modified to accommodate the gate member FIG. 8.

FIG. 10 is a view in perspective showing an alternative gate member construction;

FIG. 11 is a view in section similar to FIG. 6 but showing a control chamber which is modified in construction to accommodate the gate member of FIG. 10;

FIG. 12 is a view in section taken from the side of the valve showing the gate member and the control chamber of FIGS. 10 and 11;

FIGS. 13 (*a*), 13 (*b*), 13 (*c*), 13 (*d*) are diagrammatic illustrations showing different relative positions of the gate member and control chamber in the valve of the present invention.

FIG. 14 is a view in perspective of an alternative construction for the gate member for the present invention;

FIG. 15 is a view in section similar to FIG. 12 showing the gate member of FIG. 14 employed in a suitably provided control chamber;

FIG. 16 (*a*) and FIG. 16 (*b*) are detailed views in section showing the gate member in different positions in the control chamber;

FURTHER DESCRIPTION OF PREFERRED EMBODIMENTS

Figure 1:
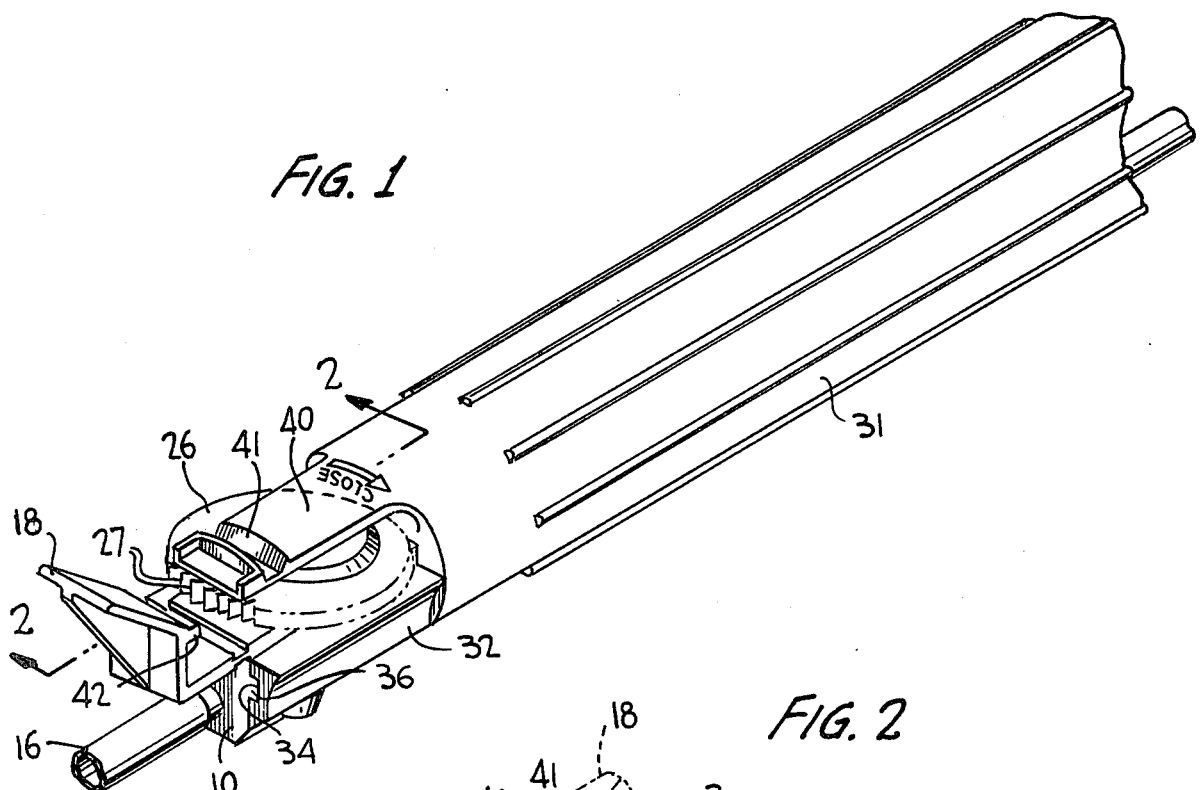
FIG. 1 is a view in perspective of a valve embodiment according to the present invention.
Figure 2:
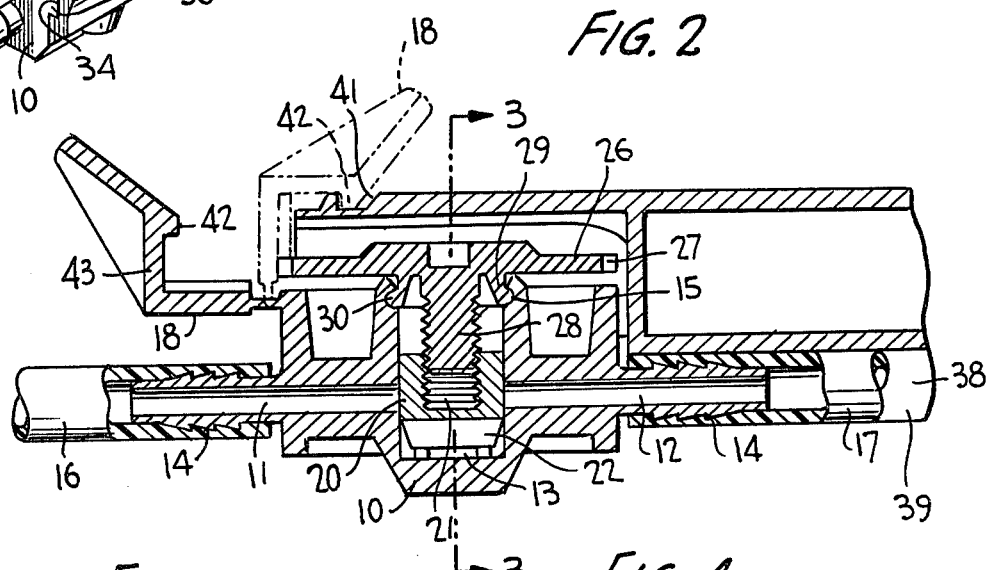
FIG. 2 is a view in section taken along lines 2—2 of FIG. 1.
Figure 3:
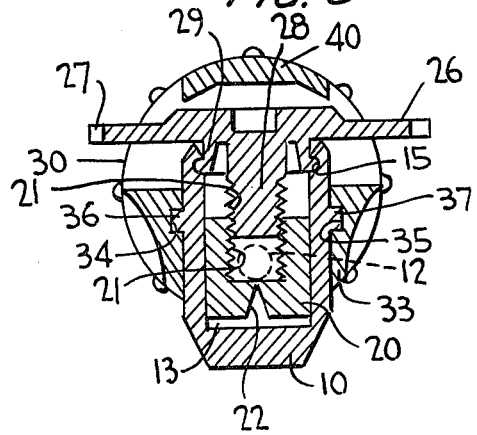
FIG. 3 is a view in section taken along lines 3—3 of FIG. 2, illustrating the valve fully closed.
Figure 4:
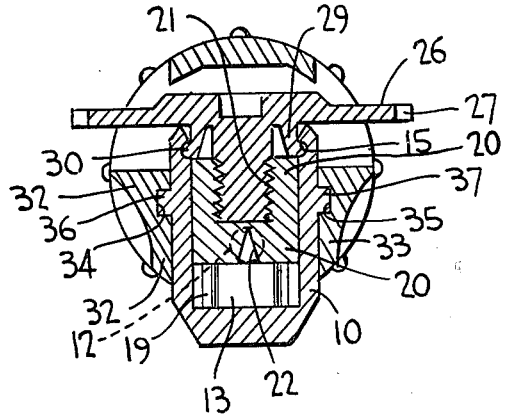
FIG. 4 is a view in section similar to that of FIG. 3 but showing the valve fully open.

Referring specifically to FIGS. 1 through 7 of the accompanying drawings, a valve body 10 is provided with the flow passages 11 and 12 of circular cross section defined as respective bores in the valve body and extending in coaxial alignment from circular openings in opposite sides of a control chamber 13. Generally tubular portions of body member 10, containing outward extensions of passages 11 and 12, are provided with barbed fittings 14 so as to be received within respective flow tubes 16 and 17. These tubes 16 and 17 are part of an I.V. set and carry parenteral liquid to and from the valve body. The flow rate of this fluid through body 10 is adjustable within control chamber 13. The control chamber takes the form of a generally cylindrical recess having an open end through which control is achieved. A plurality of annularly spaced detent numbers 19 project a short distant radially inward from the chamber wall and extend longitudinally along that wall to serve as slide guides for the valve gate member described below. A locking tab 18 is formed integrally with body member 10 and is flexibly attached to the body member so as to be movable between an open position illustrated in solid lines in FIG. 2 and a closed or locked position illustrated in dashed lines in FIG. 2. The control chamber 13 has an enlarge diameter portion at its open end wherein an annular recess 15 is defined.

A valve gate member 20 has generally cylindrical configuration and is configured to slide longitudinally in control chamber 13. To this end the gate member outerdiameter is substantially equal to the innerdiameter of the control chamber so as to provide a slidable fit. In addition, the periphery of gate member 20 is provided with a plurarlity of longitudinally-extending recesses 23 which are spaced to match and slidably receive respective detent members 19 which extend from the chamber wall. Gate member 20 has a radially-centered threaded bore 21 closed at one end and extending longitudinally therein. When the gate member is properly inserted in control chamber 13, the open end of threaded bore 21 faces the open end of the control chamber. The outer surface of the closed end of gate member 20 has a notch 22 of a generally V-shaped cross-section extending diametrically thereacross. When the gate member is properly positioned in control chamber 13, notch 22 extends parallel to passages 11 and 12 so that it may selectively change the flow communication area between passages 11 and 12 through chamber 13. In order to assure proper orientation of notch 22 when gate member 20 is inserted into chamber 13, the annular spacing between detent members 19 and between matching recesses 23 can be made non-uniform to provide a key arrangement which establishes only one or two possible mutual rotational orientations.

An adjustment member takes the form of a flat circular 26 having multiple radially-extending notches 27 formed about its circumference. A threaded stem 28 is formed integrally with and extends perpendicularly from one side of the disc along the disc central axis. The threads on stem 28 match those in bore 21 of the gate member so that stem 28 can be longitudinally inserted into and retracted from the gate member by effecting mutual rotation between disc and gate member. Also integrally formed with the disc 26 is an annular skirt 29 which projects from the same side of the disc as stem 28 and which is concentrically disposed about the proximal portion of the stem. The circumference of skirt 29 near its extremity is provided with an annular protuberance 30 which is adapted to be received in annular recess 15 and chamber 13 in a snap-fit engagement. This engagement provides a suitable hermetic seal for the control chamber interior against contamination which might otherwise enter the open chamber end. On the other hand, the annular engagement of protuberance 30 in recess 15 permits mutual rotation between the disc/-stem adjustment unit and gate member 20 while preventing axial movement of the disc/stem adjustment unit relative to chamber 13 and body member 10. The gate member 20, however, is not prevented from moving longitudinally within chamber 13, so that as disc 26 is rotated, gate member 20 rides longitudinally up or down the axially restrained stem 28. Movement of the gate member longitudinally in chamber 13 exposes more or less area of notch 22 to flow between passages 11 and 12, thereby permitting variation of the flow rate through the valve as disc 26 is rotated.

A fourth separate part of the valve assembly is handle member 31 which is a generally cylindrical elongated member having a receiving portion at one end for body member 10. This body member receiving portion includes a pair of parallel spaced similar arm members 32, 33 between which the body member is inserted with passages 11 and 12 extending parallel to the arm members. The mutually presented surfaces of arm members 32 and 33 are provided with respective channels 34 and 35 running along the length of the arm members. Channels 34, 35 are contoured to receive respective tracks 36, 37 extending along oppposite sides of the body member 10, so that the body member 10 can be slid into the handle member 31. The handle member further includes a guide section 38 which retains a flow tube 17 and the portion of barbed fitting 14 surrounding flow passage 12 which resides in tube 17. Guide section 38 is generally cylindrical with a slot 39 defined longitudinally along its periphery to permit insertion and removal of tube 17.

Handle member 31 further includes a latch portion 40 which overlies the disc 26 and includes a latch channel 41 defined in its periphery. Channel 41 is adapted to receive in resilient engagement a latch projection 42 which is an integral part of locking tab 18. Latch projection 42 can be inserted into channel 41 and retained therein when tab 18 is moved to a locked or closed position. When the latch is inserted in the channel, a bearing surface 43 on tab 18 presses against the periphery of disc 26 to hold the disc in place and prevent inadvertent rotation thereof. To this end, bearing surface 43 may be provided with ridges to mesh with the presented notches 27 defined in disc 26 to lock the disc in position.

The gate member 20 and control chamber 13 may take configurations other than cylindrical. For example, with reference to FIGS. 8 and 9, the periphery of the gate member 50 may be polygonal and walls of control chamber 51 may be matching polygonal. In the particular example illustrated, this polygonal configuration is a square; however, any regular or irregular polygon serves the purpose. It will be noted that the polygonal configurations, per se, prevents mutual rotation between the gate member and the control chamber so that detents 19 and recesses 23 can be eliminated. In addition to its external shape, gate member 50 of FIG. 8 has a bore 52 defined therethrough instead of notch 22 which appears in gate member 20. The difference here resides in the fact that bore 52 is closed along its bottom edge whereas notch 22 is open. It will be understood that the cylindrical gate member could employ a bore instead of a notch for its control passage and that the polygonal gate member could employ a notch instead of a bore for its control passage.

The embodiment of FIGS. 10, 11 and 12 is similar to the embodiment of FIGS. 8 and 9 except that, in order to reduce the length of the control passage through the body member, the body member is formed in two longitudinal sections of different thickness. Specifically, gate member 53 has an L-shaped cross-sectional configuration with a short leg 54 having a square cross section and through which is threshold bore 55 is defined, and a long leg 56 with a rectangular cross section and through which triangular control passage 57 is defined. In effect, gate member may be looked upon as being a modified version of gate member 50 with a considerable volume of material deleted from the gate member. A long leg 56 is adapted to be inserted lengthwise into a control chamber section 58 which is configured in cross-section to match that of the long leg 56. Another control chamber section 59 receives the short leg 54 of the gate member. Gate member 53 is reciprocated back and forth in chamber section 58 and 59 by means of its threaded engagement with stem 28 at bore 55 in the same manner described above for gate member 20. Control passage 57 is thereby made to selectively vary the flow communication area between flow passages 11 and 12 disposed on opposite sides of control chamber section 58.

Gate member 61 illustrated in FIG. 14 is identical to gate member 53 of FIG. 10 except that a control passage is defined as a notch 62 in the remote edge of long leg 56 rather than as a through bore 57. In all other respects gate members 61 and 53 are the same and are used in conjunction with control chamber sections 58 and 59.

The embodiment illustrated in FIG. 15 and FIGS. 16 (a) and 16 (b) employs the gate member 61 much in the same way as it would be employed in the embodiment illustrated in FIG. 12. It will be noted, however, that the lower ends of the front end rear wall chamber 59' in FIGS. 15, 16 (a) and 16 (b) converge. This causes the resilient long leg 56 to be squeezed as it is lowered into the chamber so that the notch passage is gradually closed off. This has the effect of varying the flow rate versus gate position characteristic of the valve from that which exists without pinching off of the control passage. The flow area is, in effect, varied in two dimensions with this embodiment, even though the gate member is moved in only one dimension.

The operation of the valve as illustrated by the sequential diagrammatic representations in FIGS. 13 (a) through 13 (d). These figures show a triangular bore 70 formed in gate member 71 and moving relative to a flow passage 11 in control chamber 72. Although the bore-type control passage is illustrated in these figures, the same operational theory described below applies to a notch-type control passage, such as notch 22 or notch 62. In FIG. 13 (d) the triangular control passage 70 is shown totally out of alignment with flow passage 11. In this position, flow between passages 11 and 12 is blocked and the valve is closed. As the gate memberis moved upward (in the orientation illustrated in the drawings) a small portion of the upper angle of the triangular passage begins to register with passage 11 as illustrated in FIG. 13 (c). Further movement of the gate members 71 in this direction exposes more and more of the area of control passage 70 to flow passage 11 and thereby increases the flow rate through the valve as illustrated sequentially in FIGS. 13 (b) and 13 (a). Importantly, the triangular control passage 70 must be oriented so that an angle, rather than a single side, of the triangular control passage 70 makes first registration with passage 11 as the valve is gradually opened. This permits the desired gradual control over low flow rates. If the triangular control passage is an isoceles triangle disposed symmetrically about an axis extending in the direction of gate member movement and passing through a diameter of the flow passage 11, the flow area versus gate member position characteristic takes the form of a parabola, as described below in relation to FIG. 18. If the flow through the valve is laminar (i.e. low Reynolds numbers) as would be expected in the flow rates of interest for intravenous liquid administration, the flow area presented by the exposed portion of the control passage 70 is proportional to the flow rate through the valve. Therefore, the flow rate versus gate member position is also parabolic.

Figure 17:
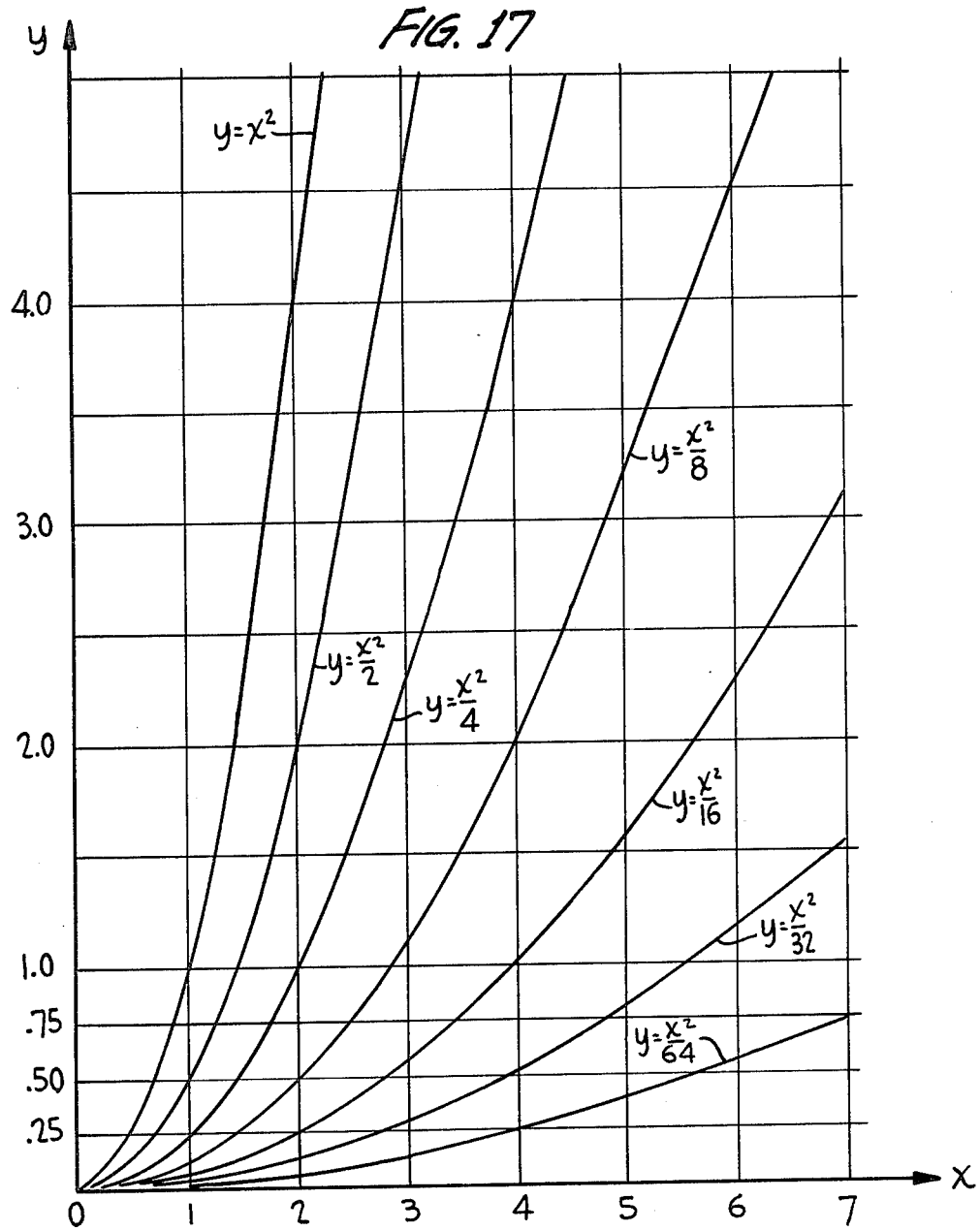
FIG. 17 is a family of parabolic curves representing possible flow rate vs. valve setting characteristics of the valve of the present invention.

The value of a parabolic function for the flow rate versus gate member position characteristic may be noted from FIG. 17 wherein seven different parabolic functions are illustrated. These functions are designated as follows: $Y = x$; $y = x^2/2$; $y = x^2/4$; $y = x^2/8$; $y = x^2/16$; $y = x^2/32$; $y = x^2/64$. It is noted that, as the coefficient of $x^2$ decreases, the value of y increases much more slowly as a function of x. X represents the valve gate member position, and the y represents the flow rate through the valve. It can be seen that the flow rate can be controlled quite closely over a wide range of valve position adjustments if the coefficient of $x^2$ is properly selected. Moreover, in the range of interest, the parabolic function approximates a linear function of y vs. x to a sufficient degree for I.V. flow control applications. It will be also noted that once the value of x increases beyond the low valve control range, y increases greatly as x is further increased. This, then, permits the valve position (x) to be rapidly changed to achieve a very large flow rate (y) through the valve for purposes of valve purging, etc.

Figure 18:
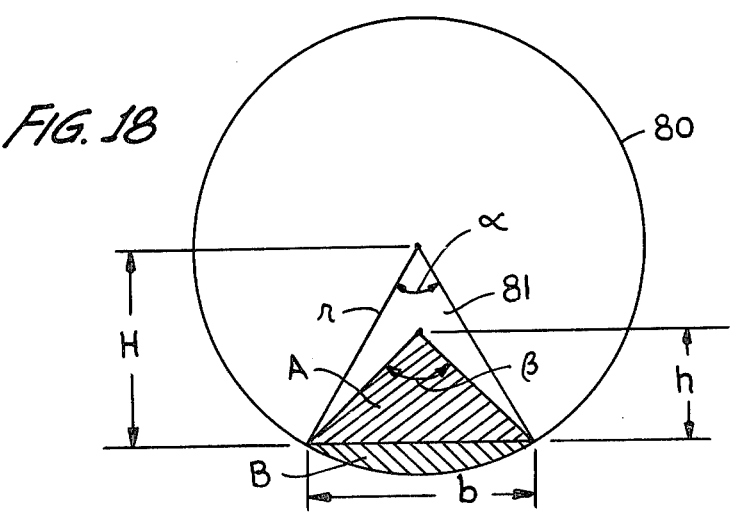
FIG. 18 is a diagram employed in conjunction with a mathematical analysis of the valve operation described herein.

In order to illustrated the nature of the parabolic function provided by the valve of the present invention, reference is made to FIG. 18. The circle 80 diagrammatically represents the cross-section of the flow passage 11 in the valve of present invention. The area exposed between flow passages 11 and 12 by the valve control passage (i.e. notches 22, 62; bores 52, 57) at any time is represented by the triangular area A plus the area B of the segment of circle 80 cut by the base b of triangular area A. Note that b is defined as the line joining the portions of the equal legs of the control passage from the points at which these legs intersect the circle 80. Thus, the exposed flow area S may be represented as follows:

$$F = A + B \tag{1}$$

Area A, on the other hand, may be represented as:

$$A = (bh)/2 \tag{2}$$

where b is the base and h is the height of the triangle A. The area B of the segment of the circle may be represented as the difference between the area of the circle within the central angle $\alpha$ (formed by radii r extending from the circle origin to the points of intersection of the circle with the sides of triangle A) less the area of a triangle 81 formed by radii r subtending central angle $\alpha$ and joining at their intersection with the circle 80. Area B may thus be represented mathematically as follows $$B = \frac{\alpha \pi r^2}{360} - \frac{bH}{2}, \tag{3}$$

where H is the height of the triangle 81. It can be further shown that $$\alpha = 2 \sin^{-1} \frac{b}{2r} \tag{4}$$

and $$H = r \cos \frac{\alpha}{2}. \tag{5}$$

Substituting for $\alpha$ from equation (4) in equation (5), $$H = r \cos (\sin^{-1}) \frac{b}{2r}. \tag{6}$$

Then, substituting the value H from equation (6) into equation (3), and further substituting the values of A and B from equations (2) and (3) into equation (1), $$F = \frac{bh}{2} + \frac{2\pi r^2}{360} \sin^{-1} \frac{b}{2r} - \frac{br}{2} \cos \left( \sin^{-1} \frac{b}{2r} \right). \tag{7}$$

Since h is a direct measure of the position of the valve control passage relative to the control passage, it is convenient to represent F in terms of h without b. It will be seen that $$b = 2h \tan (\beta)/2 \tag{8}$$

where $\beta$ is the fixed angle between the equal sides of the control passage. Since $\beta$ is fixed, then $2 \tan \beta/2$ is a constant and can be represented by m, whereby $$b = mh. \tag{9}$$

Substituting this value of b into equation (7)

$$F = \frac{mh^2}{2} + n\sin^{-1} \frac{mh}{2r} - ph\cos \left( \sin^{-1} \frac{mh}{2r} \right), \tag{10}$$

where $n = \frac{2\pi r^2}{360}$ and $p = \frac{mr}{2}$.

The dominant term in equation (10) is the $(mh^2)/2$ which renders F a substantially parabolic function of h. For very small values of h, the last two terms cancel each other so that the parabolic function is even truer in this range. In view of the discussions set forth above concerning FIG. 17, if m is varied, the range of accurate control of flow rate (F) with changing valve position (h) can be adjusted. Since m is proportional to $\beta$, then m is selected by selecting $\beta$ which is the angle between the equal legs in the control passage. More specifically, the accurate control range is extended as $\beta$ is decreased. In an actual embodiment according to FIGS. 1–7 which was constructed and successfully tested, the notch 22 was 0.077 inches deep and 0.025 inches wide at its widest point. The diameter of passages 11 and 12 was 0.088 inches. The threads of stem 28 and bore 21 numbered 32 to the inch. Smooth adjustment of flow rates between 1 and 4 cc per minute were easily achieved with this embodiment. The test was conducted with water. Additional tests showed that higher viscosity fluids exhibit similar relationships with the slope of the curves being essentially the same, due to the belief that viscosity does not adversely affect the parabolic function primarily because of the low flow rate employed in I.V. systems. The tests also showed that, while the flow rates increase with increasing supply pressure, the slopes of the curves remain the same or substantially the same.

An important feature of the valve resides in the fact that the valve opening for flow rates as low as 1 cc per minute is substantially larger than that allowable for particulates in parenteral fluid. Specifically, the valve opening for the example setforth above is approximately 0.003 inches whereas the permissible size of parenteral fluid particulates is 0.001 inches. Therefore, there is little danger of the opening being clogged by particulates in the fluid.

The valve described herein has only 4 easily manufactured parts and yet permits excellent control accuracy for flow rate adjustment over the low flow rate range. The parts can be made of plastic, metal, or other suitable material consistent with the operation and functions described herein. Notch 22 or bore 52 can easily be formed as part of a molding process.

While I have described and illustrated various specific embodiments of my invention, it will be clear that variations from the details of construction which are specifically illustrated and described may be resorted to without departing from the true spirit and scope of the invention as defined in the following claims.

I claim:

1. A valve for controlling fluid flow through intravenous supply tubing comprising:
    a valve body having a control tube, a fluid inlet passage and a fluid outlet passage defined therein, said inlet and outlet passages providing flow communication from outside said valve body to respective first and second openings in said control chamber, wherein said valve body has additionally defined therein a control opening communicating from outside said body to said control chamber;
    a gate member disposed for slidable movement in said control chamber between a first position in which it blocks flow communication between said first and second openings through said control chamber and a second position in which it provides a maximum flow communication between said first and second openings through said control chamber, said gate member having a control passage defined therethrough for providing gradually increasing flow communication between said first and second openings as said gate member slides from said first position to said second position, wherein said first and second openings have a first transverse cross-section and said control passage has a second different transverse cross section;
    control means disposed at said control opening for selectively sliding said gate member over a continuous range of positions between said first and second positions;
    wherein said control chamber has first and second longitudinal sections, said first section having a greater cross-sectional area than said second section, said second section taking the form of a longitudinally-extending slot, wherein said first and second openings are disposed in alignment in opposite sides of said chamber across the smallest dimensions of said slot;
    wherein said gate member includes a first portion which is slidably received in said second control chamber section, said control passage being defined in said second portion of said gate member;
    wherein said control chamber includes a chamfered portion at one end which is contoured to compress said gate member and constrict said control passage as the gate member slides toward said first position.

2. The valve according to claim 1 wherein said valve has a flow communication verses gate member position characteristic in which the flow communication first increase is relatively slowly and then relatively rapidly as the gate member slides from said first position to said second position, wherein said first cross-section is circular and said second cross-section is triangular, and wherein said triangular second cross-section has an apex pointing toward said second position and a side opposite said apex oriented substantially perpendicular to the slide direction of said gate member.

3. A valve for controlling fluid flow through intravenous supply tubing comprising:
    a valve body having a control tube, a fluid inlet passage and a fluid outlet passage defined therein, said inlet and outlet passages providing flow communication from outside said valve body to respective first and second openings in said control chamber, wherein said valve body has additionally defined therein a control opening communicating from outside said body to said control chamber;
    a gate member disposed for slidable movement in said control chamber between a first position in which it blocks flow communication between said first and second openings through said control chamber and a second position in which it provides a maximum flow communication between said first and second openings through said control chamber, said gate member having a control passage defined therethrough for providing gradually increasing flow communication between said first and second openings as said gate member slides from said first position to said second position, wherein said first and second openings have a first transverse cross-section and said control passage has a second different transverse cross section; and
    control means disposed at said control opening for selectively sliding said gate member over a continuous range of positions between said first and second positions;
    wherein said control chamber includes a chamfered portion which is contoured to compress said gate member and constrict said control passage as the gate member slides toward said first position.

4. The valve according to claim 3 wherein said valve has a flow communication versus gate member position characteristic in which the flow communication first increases relatively slowly and then relatively rapidly as the gate member slides from said first position to said second position.

5. The valve according to claim 4 wherein said first cross-section is circular and said second cross-section is triangular.

6. The valve according to claim 4 wherein said first cross-section is circular and said second cross-section tapers toward said second position.

7. The valve according to claim 5 wherein said second cross-section is a triangle having an apex pointing toward said second position and a side opposite said apex oriented substantially perpendicular to the slide direction of said gate member.

8. The valve according to claim 3 wherein the control chamber has a polygonal cross-section through which a longitudinal axis perpendicularly extends, wherein said first and second openings are aligned diametrically across said control chamber, and wherein said gate member has a periphery with the same polygonal configuration as the chamber of cross-section.

9. The valve according to claim 8 wherein the control passage is a V-shaped groove defined transversely across on surface of said gate member.

10. The valve according to claim 8 wherein the control passage is a bore defined transversely through said gate member.

11. The valve according to claim 3 wherein said control means comprises a disc member disposed outside said chamber, and a threaded stem projecting co-axially from said disc member into said control opening; wherein said gate member includes a threaded bore arranged to threadedly engage said stem inside said chamber; and further comprising attachment means for securing said disc member to said body for selective rotation of said disc member and stem relative to said body while preventing axial movement of said disc member and stem, whereby rotation of said disc causes said stem to rotate in its threaded engagement with the gate member to translate the gate member in the control chamber.

12. The valve according to claim 11 wherein said attachment means comprises an annular snap-fit engagement between said control means and said body.

13. The valve according to claim 12 wherein said annular snap-fit engagement comprises:
an annular flange having slight radial compressibility projecting from said disc member in concentric relation about such stem.

14. The valve according to claim 13 further comprising locking means for selectively locking the rotational position of said disc relative to said body.

15. The valve according to claim 14 further comprising a handle member including means for engaging said body, and wherein said locking means includes:
a bearing surface of a flexible member formed as part of said body and including a first mating element;
and a second mating element comprising an integral part of said handle for selectively engaging said first mating element.

* * * * *